United States Patent
Cao et al.

(10) Patent No.: US 7,008,610 B2
(45) Date of Patent: Mar. 7, 2006

(54) AEI-TYPE ZEOLITE, ITS SYNTHESIS AND ITS USE IN THE CONVERSION OF OXYGENATES TO OLEFINS

(75) Inventors: Guang Cao, Branchburg, NJ (US); Karl G. Strohmaier, Port Murray, NJ (US); Hailian Li, Sunnyvale, CA (US); Anil S. Guram, San Jose, CA (US); Robert J. Saxton, Pleasanton, CA (US); Mark T. Muraoka, Mountain View, CA (US); Jeffrey C. Yoder, San Jose, CA (US); Karin Yaccato, Cambridge, MA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/017,091

(22) Filed: Dec. 20, 2004

(65) Prior Publication Data

US 2005/0197519 A1   Sep. 8, 2005

Related U.S. Application Data

(60) Provisional application No. 60/532,596, filed on Dec. 23, 2003.

(51) Int. Cl.
*C01B 39/48* (2006.01)

(52) U.S. Cl. .................. 423/706; 423/709; 423/713; 549/640

(58) Field of Classification Search ............... 423/706, 423/709, 713, DIG. 30; 585/640
See application file for complete search history.

(56) References Cited

U.S. PATENT DOCUMENTS

| | | | | |
|---|---|---|---|---|
| 5,095,163 A | | 3/1992 | Barger | ........................ 585/640 |
| 5,958,370 A | | 9/1999 | Zones et al. | ................ 423/706 |
| 6,153,798 A | * | 11/2000 | Hidaka et al. | .............. 564/479 |

OTHER PUBLICATIONS

Abstract—"Synthesis of Novel Zeolites SSZ-53 Using Novel Organic Templating Agents Derived From Nitriles", Studies in Surface Science and Catalysis (2001), 135 (Zeolites and Mesoporous Materials at the Dawn of the 21st Century), 479-486.
Guest/Host Relationships in the Synthesis of the Novel Cage-Based Zeolites SSZ-35, SSZ-36 and SSZ-39, J. Am. Chem. Soc. 2000, 122 (2), pp. 263-273.

* cited by examiner

*Primary Examiner*—David Sample

(57) ABSTRACT

A crystalline material is described that has an AEI framework type, wherein the material, in its calcined, anhydrous form, has a composition involving the molar relationship:

$$(n)X_2O_3:YO_2,$$

wherein X is a trivalent element, Y is a tetravalent element n is from 0 to less than 0.01. The material is normally synthesized in a halide, typically a fluoride, medium and exhibits activity and selectivity in the conversion of methanol to lower olefins, especially ethylene and propylene.

47 Claims, 2 Drawing Sheets

AEI-TYPE ZEOLITE, ITS SYNTHESIS AND ITS USE IN THE CONVERSION OF OXYGENATES TO OLEFINS

CROSS REFERENCE TO RELATED APPLICATIONS

This application claims priority to Provisional Application No. 60/532,596, filed Dec. 23, 2003, the disclosures of which are incorporated by reference.

FIELD OF INVENTION

This invention relates to a zeolite having an AEI framework type, its synthesis and its use in the conversion of oxygenates, particularly methanol, to olefins, particularly ethylene and propylene.

BACKGROUND OF INVENTION

The conversion of oxygenates to olefins (OTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. OTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are eight-membered ring aluminosilicates, such as those having the chabazite (CHA) framework type, as well as silicoaluminophosphates of the CHA structure, such as SAPO-34. These molecular sieves have cages that are sufficiently large to accommodate aromatic intermediates while still allowing the diffusional transport of reactants and products into and out of the crystals through regularly interconnected window apertures. By complementing such morphological characteristics with appropriate levels of acid strength and acid density, working catalysts are produced. Extensive research in this area indicates that silicoaluminophosphates are currently more effective OTO catalysts than aluminosilicates. In particular, the control of the silica to alumina molar ratio is a key requirement for the use of aluminosilicates in OTO reactions. Nevertheless, aluminosilicate zeolites continue to be explored for use in OTO and appear to have yet undiscovered potential.

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the *Atlas of Zeolite Framework Types*, 5th edition, Elsevier, London, England (2001).

One known molecular sieve for which a structure has been established is the material designated as AEI, which is a molecular sieve having pores defined by two sets of generally perpendicular channels each having a cross-sectional dimension about 3.8 Angstrom. Molecular sieves of the AEI framework type do not exist in nature, but a number of aluminophosphates and silicoaluminophosphates having the AEI framework type have been synthesized, including SAPO-18, ALPO-18 and RUW-18. Moreover, because of their small pore size, AEI-type molecular sieves have been reported as suitable catalysts for a variety of important chemical processes, including the conversion of oxygenates to olefins. See, for example, U.S. Pat. No. 5,095,163, incorporated herein by reference.

Zones et al., U.S. Pat. No. 5,958,370, incorporated herein by reference, discloses an aluminosilicate zeolite designated SSZ-39 and having a silica to alumina molar ratio greater than 10, such as 10 to 100. SSZ-39 is produced by crystallizing an aqueous mixture comprising active sources of a trivalent element, such as aluminum, and a tetravalent element, such as silicon, in the presence of certain cyclic or polycyclic quaternary ammonium cations, such as N,N-dimethyl-2,6-dimethylpiperidinium cations, as templating agents. The synthesis can be conducted in the presence of SSZ-39 seed crystals, but there is no disclosure of the presence of fluoride ions in the synthesis mixture.

The highest silica to alumina ratio exemplified for SSZ-39 in the Zones et al. patent is 51. Moreover, in column 5, lines 56 to 61, Zones et al. teach that SSZ-39 can be synthesized directly only as an aluminosilicate, although suggest that the silica to alumina mole ratio can be increased, potentially to produce an essentially aluminum-free material, by use of standard acid leaching or chelating treatments. However, as is shown in the Comparative Example 13 below, attempts to dealuminize SSZ-39 by acid leaching or chelation have met with only limited success and have failed to produce materials having a silica to alumina ratio greater than 100.

In an article entitled "Guest/Host Relationships in the Synthesis of the Novel Cage-Based Zeolites SSZ-35, SSZ-36 and SSZ-39", J. Am. Chem. Soc., 2000, 122, pages 263–273 Zones and certain of the co-inventors from U.S. Pat. No. 5,958,370 discuss the synthesis and structure of the molecular sieves, SSZ-35, SSZ-36 and SSZ-39. According to this article SSZ-39 is isomorphous with the AEI framework type aluminophosphate molecular sieve SAPO-18 and is a frequently observed product of high-alumina containing syntheses using cyclic and polycyclic quaternized amine structure directing agents. In particular, the article reports that, although SSZ-39 is produced at silica to alumina mole ratios of 30 with a variety of directing agents, including N,N-dimethyl-2,6-dimethylpiperidinium compounds, when the silica to alumina mole ratio is increased to 40 or higher, other crystalline phases, such as SSZ-35 and MFI and MTW framework type materials, are produced.

Aluminosilicates having a silica to alumina ratio greater than 100 and all-silica molecular sieves with an AEI framework-type have so far not been reported.

The present invention relates to the composition and synthesis of a novel high silica zeolite having the AEI framework-type, its homologues in which the silicon is partly or wholly replaced by other tetravalent elements and its various uses, including in the conversion of olefins to oxygenates.

SUMMARY

In one aspect, the invention resides in a crystalline material having an AEI framework type, wherein said material, in its calcined, anhydrous form, has a composition involving the molar relationship:

$$(n)X_2O_3{:}YO_2,$$

wherein X is a trivalent element, such as aluminum, boron, iron, indium, and/or gallium; Y is a tetravalent element such as silicon, tin, titanium and/or germanium; and n is from 0 to less than 0.01, such as from about 0.001 to less than 0.01, for example from about 0.0025 to about 0.008, typically from about 0.003 to about 0.007.

Conveniently, the calcined crystalline material contains from about 1 to about 100 ppm, for example from about 5 to about 50 ppm, such as from about 10 to about 20 ppm, by weight of a halide, preferably fluoride.

In another embodiment, the crystalline material is substantially free of framework phosphorus.

In a further aspect, the invention resides in a method of synthesizing a crystalline material having an AEI framework type and comprising $YO_2$ and optionally $X_2O_3$ wherein X is a trivalent element and Y is a tetravalent element, the method comprising:
  (a) preparing a reaction mixture capable of forming said material, said mixture comprising a source of water, a source an oxide of the tetravalent element Y, optionally a source an oxide of the trivalent element X and an organic directing agent for directing the formation of said crystalline material;
  (b) maintaining said reaction mixture under conditions sufficient to form crystals of said crystalline material comprising a composition involving the molar relationship:

$$(n)X_2O_3{:}YO_2,$$

where n is from 0 to less than 0.01; and
  (c) recovering said crystalline material from (b).

Conveniently, said reaction mixture also comprises a halide or a halide-containing compound, such as a fluoride or a fluoride-containing compound.

In one embodiment, said organic directing agent comprises a cyclic amine or ammonium compound, such as a N-substituted piperidinium compound, for example a tetraalkylpiperidinium compound, typically a N,N-diethyl-2,6-dimethylpiperidinium compound.

Conveniently, said reaction mixture also comprises seed crystals, such as seed crystals comprising a microporous crystalline aluminosilicate having an AEI, CHA, OFF or LEV framework type.

In still a further aspect, the invention resides in a process for producing olefins comprising the step of contacting an organic oxygenate compound under oxygenate conversion conditions with a catalyst comprising a crystalline material having an AEI framework type, wherein said material, in its calcined, anhydrous form, has a composition involving the molar relationship:

$$(n)X_2O_3{:}YO_2,$$

wherein X is a trivalent element, Y is a tetravalent element and n is from 0 to less than 0.01, such as from about 0.001 to less than 0.01, for example from about 0.0025 to about 0.008, typically from about 0.003 to about 0.007.

It is to be understood that the term "in its calcined, anhydrous form" is used herein to refer to a material which has been heated in air at a temperature in excess of 400° C. for 0.1 to 10 hours without allowing the material to rehydrate.

DETAILED DESCRIPTION OF THE EMBODIMENTS

Figure 1:
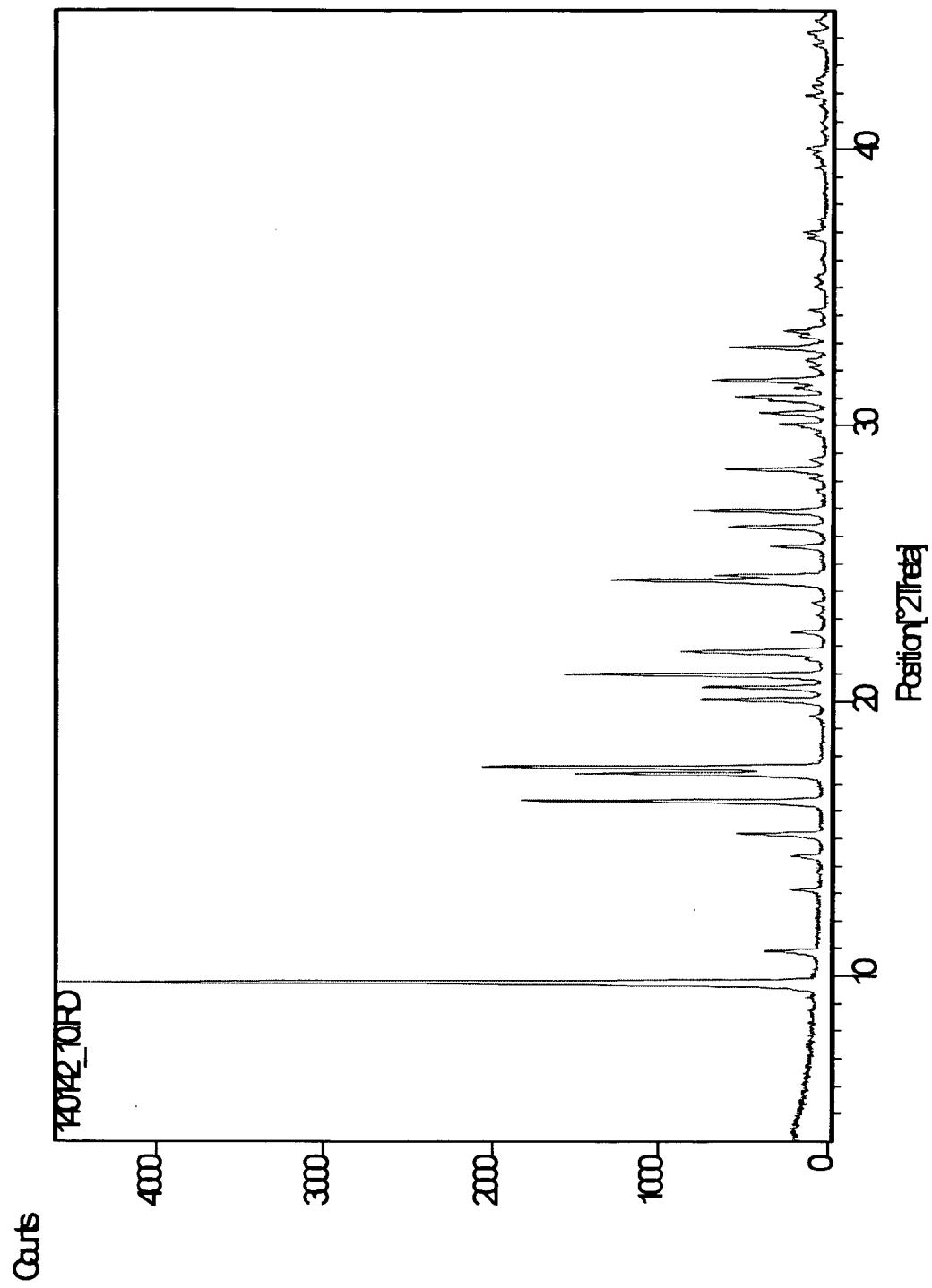
FIG. 1 is an X-ray diffraction pattern of the as-synthesized product of Example 1.

The present invention relates to a novel crystalline material having an AEI framework type and to its synthesis, particularly in a fluoride medium. In addition, the invention relates to the use of this novel crystalline material, such as in a process for the conversion of oxygenates, particularly methanol, to olefins, particularly ethylene and propylene.

In its calcined and anhydrous form, the AEI framework-type crystalline material of the present invention is porous and has a composition involving the molar relationship:

$$(n)X_2O_3{:}YO_2,$$

wherein X (if present) is a trivalent element, such as aluminum, boron, iron, indium, gallium or a combination thereof, typically aluminum; Y is a tetravalent element, such as silicon, tin, titanium, germanium or a combination thereof, typically silicon; and n is from 0 to less than 0.01, such as from about 0.001 to less than 0.01, for example from about 0.0025 to about 0.008, typically from about 0.003 to about 0.007. Where a halide-containing compound has been used in the synthesis of the material, the calcined form of the AEI framework-type crystalline material of the present invention is normally found to contain trace amounts, typically from about 1 to about 100 ppm, for example from about 5 to about 50 ppm, such as from about 10 to about 20 ppm, by weight of the halide, preferably fluoride.

In one embodiment, the AEI framework-type crystalline material of the present invention is substantially free of framework phosphorus.

In its as-synthesized form, the AEI framework-type crystalline material of the present invention has a composition involving the molar relationship:

$$(n)X_2O_3{:}YO_2{:}(m)R{:}(x)F{:}z\ H_2O,$$

wherein X, Y and n are as defined in the preceding paragraph, R is at least one organic directing agent and wherein m ranges from about 0.01 to about 2, such as from about 0.1 to about 1, z ranges from about 0.5 to about 100, such as from about 2 to about 20 and x ranges from about 0 to about 2, such as from about 0.01 to about 1. The R and F components, which are associated with the material as a result of their presence during crystallization, are at least partly removed by post-crystallization methods hereinafter more particularly described. Typically, the as-synthesized AEI framework-type crystalline material of the present invention contains only low levels of alkali metal, generally such that the combined amount of any potassium and sodium is less than 50% of the $X_2O_3$ on a molar basis. For this reason, after removal of the organic directing agent (R), the material generally exhibits catalytic activity without a preliminary ion-exchange step to remove alkali metal cations.

To the extent desired and depending on the $X_2O_3/YO_2$ molar ratio of the material, any cations in the as-synthesized AEI framework-type material can be replaced in accordance with techniques well known in the art, at least in part, by ion exchange with other cations. Preferred replacing cations include metal ions, hydrogen ions, hydrogen precursor, e.g., ammonium ions, and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIIB, VIIB and VIII of the Periodic Table of the Elements.

The AEI framework-type crystalline material of the invention can be prepared from a reaction mixture containing a source of water, a source of an oxide of the tetravalent element Y, optionally a source of an oxide of the trivalent element X, at least one organic directing agent (R) as described below, and typically a halide or a halide-containing compound, such as a fluoride or a fluoride-containing compound, said reaction mixture having a composition, in terms of mole ratios of oxides, within the following ranges:

| Reactants | Useful | Typical |
| --- | --- | --- |
| $H_2O/YO_2$ | 0.1 to 20 | 2 to 10 |
| Halide/$YO_2$ | 0 to 2 | 0.01 to 1 |
| R/$YO_2$ | 0.01 to 2 | 0.1 to 1 |
| $X_2O_3/YO_2$ | 0 to 0.5 | 0 to 0.1 |

Where the tetravalent element Y is silicon, suitable sources of silicon include silicates, e.g., tetraalkyl orthosilicates, fumed silica, such as Aerosil (available from Degussa), and aqueous colloidal suspensions of silica, for example that sold by E.I. du Pont de Nemours under the tradename Ludox. Where the trivalent element X is aluminum, suitable sources of aluminum include aluminum salts, especially water-soluble salts, such as aluminum nitrate, as well as hydrated aluminum oxides, such as boehmite and pseudoboehmite. Where the halide is fluoride, suitable sources of fluoride include hydrogen fluoride, although more benign sources of fluoride such as alkali metal fluorides and fluoride salts of the organic directing agent are preferred.

The organic directing agent R used herein conveniently comprises a cyclic amine or ammonium compound, such as an N-substituted piperidinium compound, for example a tetraalkylpiperidinium compound, typically a N,N-diethyl-2,6-dimethylpiperidinium compound. Suitable compounds include hydroxides and salts, such as halides.

Conveniently, the reaction mixture has a pH of about 4 to about 14, such as about 4 to about 10, for example about 6 to about 8.

Crystallization can be carried out at either static or stirred conditions in a suitable reactor vessel, such as for example, polypropylene jars or Teflon®-lined or stainless steel autoclaves, at a temperature of about 50° C. to about 300° C., such as about 135° C. to about 175° C., for a time sufficient for crystallization to occur. Formation of the crystalline product can take anywhere from around 30 minutes up to as much as 2 weeks, such as from about 45 minutes to about 240 hours, for example from about 1.0 to about 120 hours. The duration depends on the temperature employed, with higher temperatures typically requiring shorter hydrothermal treatments.

Synthesis of the new zeolite may be facilitated by the presence of at least 0.1 ppm, such as at least 10 ppm, for example at least 100 ppm, conveniently at least 500 ppm of seed crystals based on total weight of the reaction mixture. The seed crystals can be homostructural with the crystalline material of the present invention, for example the product of a previous synthesis, or can be a heterostructural crystalline material, such as an LEV, CHA or OFF framework-type molecular sieve. The seeds may be added to the reaction mixture as a colloidal suspension in a liquid medium, such as water. The production of colloidal seed suspensions and their use in the synthesis of molecular sieves are disclosed in, for example, International Publication Nos. WO 00/06493 and WO 00/06494 published on Feb. 10, 2000 and incorporated herein by reference.

Typically, the crystalline product is formed in solution and can be recovered by standard means, such as by centrifugation or filtration. The separated product can also be washed, recovered by centrifugation or filtration and dried.

As a result of the crystallization process, the recovered crystalline product contains within its pores at least a portion of the organic directing agent used in the synthesis. Typically, therefore, the as-synthesized material is treated in manner to remove the organic directing agent from the molecular sieve, leaving active catalytic sites within the microporous channels of the molecular sieve open for contact with a feedstock. This is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system. In other cases, particularly with smaller organic directing agents, complete or partial removal from the sieve can be accomplished by conventional desorption processes.

Once the AEI framework-type crystalline material of the invention has been synthesized, it can be formulated into a catalyst composition by combination with other materials, such as binders and/or matrix materials, that provide additional hardness or catalytic activity to the finished catalyst.

Materials which can be blended with the AEI framework-type material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of crystalline material contained in the final catalyst product ranges from 10 to 90 weight percent of the total catalyst, preferably 20 to 70 weight percent of the total catalyst.

The AEI framework-type crystalline material described herein can be used to dry gases and liquids; for selective molecular separation based on size and polar properties; as an ion-exchanger; as a chemical carrier; in gas chromatography; and as a catalyst in organic conversion reactions. Examples of suitable catalytic uses of the AEI framework-type crystalline material described herein include (a) hydrocracking of heavy petroleum residual feedstocks, cyclic stocks and other hydrockrate charge stocks, normally in the presence of a hydrogenation component iselected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes, (j) catalytic reduction of nitrogen oxides and (k) synthesis of monoalkylamines and dialkylamines.

In particular, the AEI framework-type crystalline material described herein is useful in the catalytic conversion of oxygenates to one or more olefins, particularly ethylene and propylene. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as from about 0.5 $hr^{-1}$ to about 300 $hr^{-1}$, for example from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In one embodiment, the catalyst is pretreated with dimethyl ether, a $C_2$–$C_4$ aldehyde composition and/or a $C_4$–$C_7$ olefin composition to form an integrated hydrocarbon co-catalyst within the porous framework of the AEI framework-type molecular sieve prior to the catalyst being used to convert oxygenate to olefins. Desirably, the pretreatment is conducted at a temperature of at least 10° C., such as at least 25° C., for example at least 50° C., higher than the temperature used for the oxygenate reaction zone and is arranged to produce at least 0.1 wt %, such as at least 1 wt %, for example at least about 5 wt % of the integrated hydrocarbon co-catalyst, based on total weight of the molecular sieve. Such preliminary treating to increase the carbon content of the molecular sieve is known as "prepooling" and is further described in U.S. application Ser. Nos. 10/712,668, 10/712,952 and 10/712,953 all of which were filed Nov. 12, 2003 and are incorporated herein by reference.

The invention will now be more particularly described with reference to the following Examples and the accompanying drawings.

In the Examples, the X-ray diffraction data were collected with a Philips powder X-Ray Diffractometer, equipped with a scintillation detector with graphite monochromator, using copper K-alpha radiation. The diffraction data were recorded by step-scanning at 0.02 degrees of two-theta, where theta is the Bragg angle, and a counting time of 1 second for each step. The interplanar spacing, d's, were calculated in Angstrom units, and the relative intensities of the lines, $I/I_o$, where $I_o$ is the intensity of the strongest line, above background were determined by integrating the peak intensities.

EXAMPLE 1

0.143 ml of a 23.5 mg/ml aqueous solution of $Al(NO_3)_3 \cdot 9H_2O$ was added to 3.717 ml of a 0.7236 molar aqueous solution of N,N-diethyl-2,6-dimethylpiperidinium hydroxide ($DEDMP^+ OH^-$) followed by 1.200 ml of tetraethylorthosilicate. The resultant mixture was continuously stirred in a sealed container for 2 hours at room temperature until all the tetraethylorthosilicate was completely hydrolyzed. To the resultant clear solution was added 0.117 ml of a 48 wt % aqueous solution of hydrofluoric acid which immediately resulted in the production of a slurry. This slurry was further homogenized by stirring and exposure to air for evaporation of water and ethanol until a thick slurry mixture was obtained. Extra water was further evaporated from the slurry mixture under static conditions to give 1317 mg of a dry gel solid having the following molar composition:

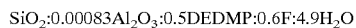

$SiO_2:0.00083Al_2O_3:0.5DEDMP:0.6F:4.9H_2O$

To this solid was added with mechanical mixing 5 mg (0.38 wt % based on the dry gel solid) of a seeding material, AEI having a Si/Al atomic ratio of 8.9 and Si/Na atomic ratio of 26.4. The resulting mixture of solids was transferred to a Teflon®-lined 5 ml pressure reactor and crystallized at 150° C. for 65 hours under slow rotation (about 60 rpm). After cooling, the resultant solid was recovered by centrifuging, washed with distilled water, and dried at 100° C. to give 373 mg of a white microcrystalline solid (28.3% yield based on the weight of the dry gel or 91.4% yield based on $SiO_2$).

Figure 2:
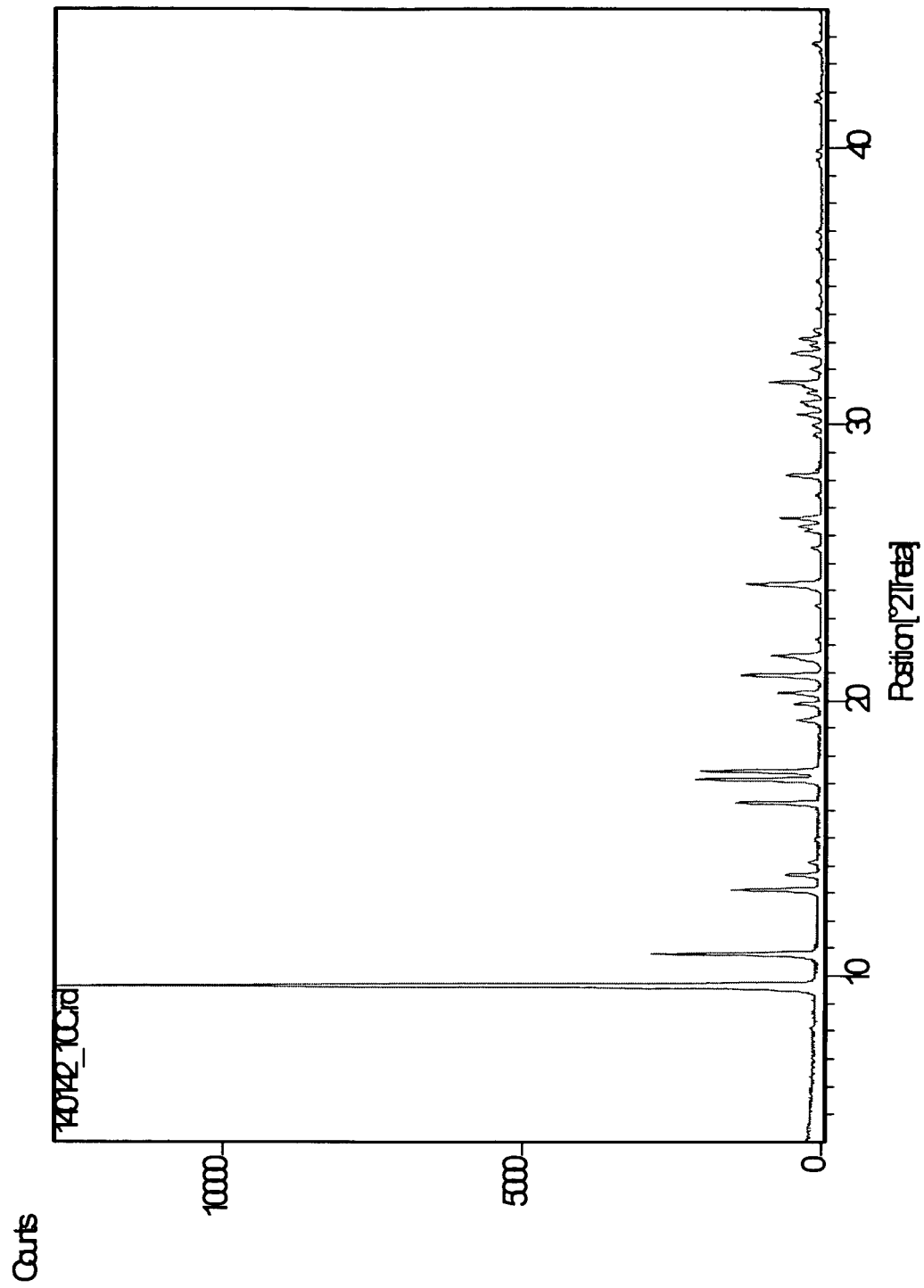
FIG. 2 is an X-ray diffraction pattern of the as-calcined product of Example 1.

The as-synthesized product had the X-ray diffraction pattern shown in FIG. 1 and summarized in Table 1 below. A portion (100 mg) of the as-synthesized product was placed in a muffle furnace and heated at 600° C. for 15 hrs in the air. The calcined material was white in appearance. The X-ray diffraction pattern for the calcined material is shown in FIG. 2 and Table 2. The X-ray data demonstrated that the material had an AEI framework-type.

TABLE 1

X-Ray Diffraction Pattern of As-Synthesized Product of Example 1

| 2 Theta | d(Å) | 100 I/Io |
|---|---|---|
| 9.77 | 9.049 | 100.0 |
| 10.90 | 8.112 | 6.7 |
| 13.13 | 6.736 | 3.8 |
| 14.35 | 6.165 | 3.6 |
| 15.16 | 5.841 | 10.8 |
| 16.37 | 5.412 | 39.3 |
| 17.36 | 5.105 | 32.5 |
| 17.59 | 5.039 | 44.6 |
| 19.45 | 4.560 | 1.4 |
| 20.06 | 4.423 | 15.9 |
| 20.51 | 4.326 | 15.5 |
| 20.97 | 4.234 | 34.2 |
| 21.79 | 4.076 | 18.4 |
| 22.51 | 3.946 | 4.1 |
| 23.56 | 3.773 | 1.3 |
| 24.39 | 3.647 | 27.6 |
| 24.56 | 3.621 | 14.1 |
| 25.63 | 3.473 | 7.0 |
| 26.34 | 3.381 | 12.2 |
| 26.92 | 3.309 | 16.7 |
| 27.62 | 3.227 | 0.7 |
| 28.43 | 3.137 | 13.1 |
| 28.77 | 3.101 | 1.9 |
| 30.05 | 2.971 | 5.9 |
| 30.46 | 2.932 | 8.2 |
| 31.04 | 2.879 | 11.7 |
| 31.39 | 2.847 | 4.0 |
| 31.65 | 2.825 | 14.8 |
| 32.39 | 2.761 | 2.4 |
| 32.84 | 2.725 | 12.4 |
| 33.25 | 2.692 | 3.3 |
| 33.43 | 2.678 | 5.5 |
| 34.20 | 2.620 | 2.2 |
| 35.05 | 2.558 | 1.4 |
| 36.79 | 2.441 | 2.2 |
| 37.00 | 2.428 | 2.3 |
| 40.03 | 2.251 | 2.7 |
| 41.92 | 2.153 | 2.4 |
| 42.22 | 2.139 | 1.8 |
| 43.74 | 2.068 | 1.6 |
| 44.15 | 2.050 | 2.4 |
| 44.59 | 2.030 | 1.6 |

TABLE 2

X-Ray Diffraction Pattern of As-Calcined Product of Example 1

| 2 Theta | d(Å) | 100 I/Io |
|---|---|---|
| 9.65 | 9.157 | 100.0 |
| 10.78 | 8.197 | 21.8 |
| 13.11 | 6.750 | 11.3 |
| 13.66 | 6.478 | 4.4 |
| 14.12 | 6.266 | 1.2 |
| 16.30 | 5.435 | 10.8 |
| 17.13 | 5.172 | 16.3 |
| 17.43 | 5.083 | 15.6 |
| 19.28 | 4.599 | 3.0 |
| 19.89 | 4.461 | 3.3 |
| 20.28 | 4.375 | 5.6 |
| 20.92 | 4.243 | 10.4 |

TABLE 2-continued

X-Ray Diffraction Pattern of As-Calcined Product of Example 1

| 2 Theta | d(Å) | 100 I/Io |
|---|---|---|
| 21.61 | 4.108 | 6.3 |
| 22.22 | 3.997 | 0.4 |
| 23.44 | 3.792 | 0.5 |
| 24.22 | 3.672 | 9.6 |
| 25.54 | 3.485 | 1.1 |
| 26.16 | 3.404 | 2.0 |
| 26.32 | 3.383 | 2.8 |
| 26.62 | 3.345 | 5.3 |
| 27.44 | 3.248 | 0.6 |
| 28.17 | 3.165 | 4.5 |
| 29.64 | 3.012 | 0.8 |
| 29.98 | 2.978 | 1.2 |
| 30.37 | 2.941 | 3.1 |
| 30.82 | 2.899 | 2.7 |
| 31.16 | 2.868 | 1.7 |
| 31.55 | 2.833 | 6.9 |
| 32.01 | 2.794 | 1.3 |
| 32.59 | 2.746 | 4.0 |
| 32.89 | 2.721 | 1.4 |
| 33.12 | 2.702 | 2.8 |
| 33.43 | 2.679 | 1.0 |
| 34.19 | 2.621 | 0.6 |
| 34.71 | 2.583 | 0.4 |
| 35.20 | 2.547 | 0.6 |
| 36.33 | 2.471 | 0.6 |
| 36.97 | 2.430 | 0.6 |
| 39.55 | 2.277 | 0.6 |
| 39.90 | 2.258 | 0.7 |
| 41.66 | 2.166 | 1.0 |
| 41.92 | 2.153 | 0.7 |
| 43.75 | 2.068 | 1.2 |

SEM analysis showed particles having a thick plate morphology and a size of about 1.5 micron thick by about 2.5 micron wide and about 2.5 micron long. EDS analysis demonstrated the as-synthesized material to contain a non-detectable (<5000 ppm) amount of alumina and to have a Si/F atomic ratio of 14.8. Elemental analysis for Si, Al, F gave Al: 0.13%; Si: 35.94%; and F: 1.54%, corresponding to a Si/Al ratio of 266 (a silica to alumina molar ratio of 532) and a Si/F ratio of 15.8 in the as-synthesized product.

EXAMPLE 2

The as-synthesized material from Example 1 was pressed to a pellet at 30,000 psig ($2.07 \times 10^5$ kPa) and then ground and sieved to between 80 and 125 μm. Two separate samples of the sized material were weighed between 21 and 22 mg and mixed separately with 90 mg of 100 μm silicon carbide. These mixtures were loaded into separate 1.9 mm internal diameter tubes sealed at the bottom with a quartz frit. The tubes were sealed into heated reactor blocks and the catalysts were then calcined at 540° C. under flowing air for 2 hours to effect organic template removal. The calcined catalysts were then subjected to methanol under a variety of conditions as detailed below.

Condition 1: The catalysts were contacted with a mixture of 85% methanol in $N_2$ at 540° C., approximately 100 weight hourly space velocity (WHSV), and 40 psia (276 kPa) methanol partial pressure. During the methanol reaction, the reactor effluents were collected and stored at timed intervals for analysis by gas chromatography. Following the methanol reaction the catalysts were subjected to a flow of 50% oxygen in nitrogen at 550° C. for approximately 90 minutes to burn off deposited coke. The reactor effluents were analyzed by infrared spectroscopy with quantitation of both carbon monoxide and carbon dioxide to determine the amounts of coke deposition.

Condition 2: The catalysts were contacted with a mixture of 73% methanol in $N_2$ at 540° C., approximately 50 weight hourly space velocity (WHSV), and 40 psia (276 kPa) methanol partial pressure. During the methanol reaction, the reactor effluents were collected and stored at timed intervals for analysis by gas chromatography. Total reaction time was 50 minutes. Following the methanol reaction the catalysts were subjected to a flow of 50% oxygen in nitrogen at 550° C. for approximately 90 minutes to burn off deposited coke. The reactor effluents were analyzed by infrared spectroscopy with quantitation of both carbon monoxide and carbon dioxide to determine the amounts of coke deposition.

Condition 3: The catalysts were contacted with a mixture of 95% methanol in $N_2$ at 450° C., approximately 400 weight hourly space velocity (WHSV), and 40 psia (276 kPa) methanol partial pressure. Total reaction time was 70 minutes. During the methanol reaction, the reactor effluents were collected and stored at timed intervals for analysis by gas chromatography. Following the methanol reaction the catalysts were subjected to a flow of 50% oxygen in nitrogen at 550° C. for approximately 90 minutes to burn off deposited coke. The reactor effluents were analyzed by infrared spectroscopy with quantitation of both carbon monoxide and carbon dioxide to determine the amounts of coke deposition.

Selectivities to a variety of hydrocarbon products were calculated for these reactions and the results are shown in Table 3. The values given below are averages of each individual selectivity over the entire reaction. Each value represents an average of the selectivities obtained from the two individual repeats.

TABLE 3

| | Condition 1 | Condition 2 | Condition 3 |
|---|---|---|---|
| $C_1$ | 1.3 | 2 | 0.6 |
| $C_2^o$ | 0.2 | 0.3 | 0.1 |
| $C_2^=$ | 26.5 | 27.3 | 18.5 |
| $C_3^o$ | 0.2 | 0.2 | 0.2 |
| $C_3^=$ | 48.6 | 47.5 | 51.1 |
| $C_4$ | 17.6 | 17.4 | 22.7 |
| $C_5^+$ | 5.1 | 4.8 | 6.4 |
| Coke | 0.4 | 0.6 | 0.7 |

EXAMPLE 3

The procedure of Example 1 was repeated but with the scale of preparation being 10 times that in Example 1, otherwise all parameters being the essentially the same. In a first preparation the hydrolysis of the tetraethylorthosilicate in N,N-diethyl-2,6-dimethylpiperidinium hydroxide was carried out for two hours, while in a second preparation the hydrolysis was for 16 hours. In the first case the resulting product was a mixture of AEI and SFF framework-types materials; whereas in the second case an essentially pure phase having the AEI framework-type was produced. The pure AEI phase had a Si/Al ratio of 233 by chemical analysis, and a thick plate morphology with a size of about 0.8 micron thick by about 1.0 micron wide and about 1.0 micron long.

EXAMPLE 4

0.429 ml of a 23.5 mg/ml aqueous solution of $Al(NO_3)_3 \cdot 9H_2O$ was added to 3.737 ml of a 0.7199 molar aqueous solution of N,N-diethyl-2,6-dimethylpiperidinium hydroxide (DEDMP⁺ OH⁻) followed by 1.200 ml of tetraethylorthosilicate. The resultant mixture was continuously stirred in a sealed container for 2 hours at room temperature until all the tetraethylorthosilicate was completely hydrolyzed. To the resultant clear solution was added 0.117 ml of a 48 wt % aqueous solution of hydrofluoric acid which immediately resulted in the production of a slurry. This slurry was homogenized by stirring and exposure to air for evaporation of water and ethanol until a thick slurry mixture was obtained. To the resultant thick slurry was added with mechanical mixing 2 mg (0.15 wt % based on the dry gel solid) of AEI seeds as a 10% mixture in water. The AEI seeds had a Si/Al atomic ratio of 8.9 and Si/Na atomic ratio of 26.4. Extra water was evaporated from the slurry mixture under static conditions to give 1141 mg of a dry gel solid having the following molar composition allowing for the seeds:

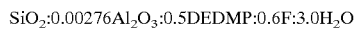

$SiO_2:0.00276Al_2O_3:0.5DEDMP:0.6F:3.0H_2O$

The resulting mixture of solids was transferred to a Teflon®-lined 5 ml pressure reactor and crystallized at 150° C. for 65 hours under slow rotation (about 60 rpm). After cooling, the resultant solid was recovered by centrifuging, washed with distilled water, and dried at 100° C. to give 372 mg of a white microcrystalline solid (32.6% yield based on the weight of the dry gel or 91.2% yield based on SiO$_2$). X-ray analysis confirmed the material to be an essentially pure phase having the AEI framework-type.

EXAMPLES 5 TO 11

The procedure of Example 4 was repeated but with the amount of the 23.5 mg/ml aqueous solution of Al(NO$_3$)$_3$·9H$_2$O being varied to produce dry gel solids having the SiO$_2$/Al$_2$O$_3$ molar compositions (allowing for the presence of the AEI seeds) as set out in Table 4.

EXAMPLE 12

The as-synthesized materials from Examples 4 to 11 were calcined as in Example 2 and the products were then contacted with a mixture of 80% methanol in N$_2$ at 400° C., a methanol partial pressure of 40 psia (276 kPa) and a weight hourly space velocity (WHSV) of about 50. The results are summarized in Table 4, which also includes the results obtained in Example 21 of U.S. Pat. No. 5,958,370 when an SSZ-39 catalyst was used to convert methanol to olefins at 400° C.

TABLE 4

| Example | SiO$_2$/Al$_2$O$_3$ gel | C$_2$ = yield, wt % | C$_3$ = yield, wt % |
| --- | --- | --- | --- |
| 4 | 362 | 13.33 | 50.35 |
| 5 | 518 | 13.66 | 51.15 |
| 6 | 660 | 13.91 | 51.06 |
| 7 | 790 | 14.19 | 51.65 |
| 8 | 1020 | 13.89 | 51.51 |
| 9 | 1122 | 14.23 | 51.93 |
| 10 | 1218 | 13.74 | 51.73 |
| 11 | 1306 | 14.30 | 51.85 |
| Example 21 of U.S. Pat. No. 5,958,370 | | 20.76 | 35.15 |

It will be seen that the crystalline materials of Example 4 to 11 each gave a considerable higher ratio of propylene yield to ethylene yield that the SSZ-39 material of in Example 21 of U.S. Pat. No. 5,958,370.

EXAMPLE 13

SSZ-39 was prepared according to U.S. Pat. No. 5,958,370 using N,N-diethyl-2,6-dimethylpiperidinium hydroxide as the organic template. Chemical analysis indicated that the SSZ-39 sample contained 2.53 wt % Al, 32.2 wt % Si and 0.28 wt % Na. The Si/Al ratio was therefore 12.2.

The SSZ-39 sample was calcined at 600° C. in air for 3 hours to remove the organic template. The calcined sample was suspended in 10% NH$_4$NO$_3$ aqueous solution twice to effect ammonium ion-exchange. The ion-exchanged sample was then subjected to steaming (700° C. for 5 hours in 100% stem under ambient pressure) to attempt to effect framework dealumination. 0.5 g of this steamed sample was further treated with 25 ml, 1N hydrochloric acid at 60° C. for 3 hours. The solid was filtered and washed thoroughly with deionized water, and dried before elemental analysis was performed. The chemical analysis indicated that the steamed and acid-leached sample contained 2.92 wt % Al, 36.0 wt % Si and 0.00% Na. The Si/Al ratio was therefore 11.8, which is essentially unchanged from that of the original sample.

Thus this example illustrates that the conventional technique of steaming and acid-leaching is ineffective for increasing the Si/Al ratio of aluminosilicate having the AEI framework type.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A crystalline material having an AEI framework type, wherein said material, in its calcined, anhydrous form, has a composition involving the molar relationship:

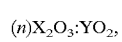

$(n)X_2O_3:YO_2,$ wherein X is a trivalent element, Y is a tetravalent element and n is from 0 to less than 0.01.

2. The crystalline material of claim 1 wherein said material is substantially free of framework phosphorus.

3. The crystalline material of claim 1 wherein n is from about 0.001 to less than 0.01.

4. The crystalline material of claim 1 wherein n is from about 0.0025 to about 0.008.

5. The crystalline material of claim 1 wherein n is from about 0.003 to about 0.007.

6. The crystalline material of claim 1 wherein X is aluminum, boron, iron, indium, gallium or a combination thereof.

7. The crystalline material of claim 1 wherein Y is silicon, tin, titanium, germanium or a combination thereof.

8. The crystalline material of claim 1 wherein X is aluminum, boron, iron, indium, gallium or a combination thereof, and Y is silicon, tin, titanium, ermanium or a combination thereof.

9. The crystalline material of claim 1 wherein Y is silicon.

10. The crystalline material of claim 1 wherein X is aluminum.

11. The crystalline material of claim 9 wherein n is zero.

12. A crystalline material having an AEI framework type, wherein said material, in its calcined, anhydrous form, has a composition involving the molar relationship:

$(n)X_2O_3:YO_2$, wherein X is a trivalent element, Y is a tetravalent element and n is from 0 to less than 0.01 and wherein said material, in its calcined form, contains from about 1 to about 100 ppm by weight of a halide.

13. The crystalline material of claim 12 wherein said material, in its calcined form, contains from about 5 to about 50 ppm by weight of a halide.

14. The crystalline material of claim 12 wherein said material, in its calcined form, contains from about 10 to about 20 ppm, by weight of a halide.

15. The crystalline material of claim 12 wherein said halide comprises fluoride.

16. The crystalline material of claim 12 wherein n is from about 0.001 to less than 0.01.

17. The crystalline material of claim 12 wherein n is from about 0.0025 to about 0.008.

18. The crystalline material of claim 12 wherein n is from about 0.003 to about 0.007.

19. A method of synthesizing a crystalline material having an AEI framework type and comprising $YO_2$ and optionally $X_2O_3$ wherein X is a trivalent element and Y is a tetravalent element, the method comprising:
   (a) preparing a reaction mixture capable of forming said material, said mixture comprising a source of water, a source an oxide of the tetravalent element Y, optionally a source an oxide of the trivalent element X and an organic directing agent for directing the formation of said crystalline material;
   (b) maintaining said reaction mixture under conditions sufficient to form crystals of said crystalline material comprising a composition involving the molar relationship:

$(n)X_2O_3:YO_2$, where n is from 0 to less than 0.01; and
   (c) recovering said crystalline material from (b).

20. The method of claim 19 wherein said reaction mixture also comprises a halide or a halide-containing compound.

21. The method of claim 19 wherein said reaction mixture also comprises a fluoride or a fluoride-containing compound.

22. The method of claim 19 wherein said organic directing agent comprises a cyclic amine or ammonium compound.

23. The method of claim 19 wherein said organic directing agent comprises a substituted piperidinium compound.

24. The method of claim 19 wherein said organic directing agent comprises a tetraalkylpiperidinium compound.

25. The method of claim 19 wherein said organic directing agent comprises an N,N-diethyl-2,6-dimethylpiperidinium compound.

26. The method of claim 19 wherein said reaction mixture has a pH of about 4 to about 10.

27. The method of claim 19 wherein said reaction mixture has the following molar composition

| | |
|---|---|
| $H_2O/YO_2$ | 0.1 to 20 |
| Halide/$YO_2$ | 0 to 2 |
| R/$YO_2$ | 0.01 to 2; |
| $X_2O_3/YO_2$ | 0 to 0.5, | where R is an organic directing agent.

28. The method of claim 19 wherein said reaction mixture has the following molar composition

| | |
|---|---|
| $H_2O/YO_2$ | 2 to 10; |
| Halide/$YO_2$ | 0.01 to 1; |
| R/$YO_2$ | 0.1 to 1; |
| $X_2O_3/YO_2$ | 0 to 0.1, | where R is an organic directing agent.

29. The method of claim 19 wherein X is aluminum and Y is silicon.

30. The method of claim 19 wherein said reaction mixture also comprises seed crystals.

31. The method of claim 30 wherein said seed crystals are added to said reaction mixture as a colloidal suspension in a liquid medium.

32. The method of claim 30 wherein said seed crystals comprise a crystalline material having an AEI, LEV, CHA or OFF framework type.

33. The method of claim 30 wherein said seed crystals comprise a crystalline material having an AEI framework type.

34. The method of claim 33 wherein the crystalline material having an AEI framework type is an aluminosilicate.

35. The method of claim 19 wherein the conditions in (b) include a temperature of from about 50° C. to about 300° C.

36. The method of claim 19 wherein the conditions in (b) include a temperature of from about 135° C. to about 185° C.

37. An organic conversion process comprising contacting an organic feedstock with a catalyst comprising a crystalline material having an AEI framework type and comprises a composition involving the molar relationship:

$(n)X_2O_3:YO_2$, wherein X is a trivalent element, Y is a tetravalent element and n is from 0 to less than 0.01.

38. The process of claim 37 wherein said feedstock comprises an oxygenate and the process comprises converting said oxygenate into an olefin product.

39. The process of claim 37 wherein said material is substantially free of framework phosphorus.

40. The process of claim 37 wherein said material, in its calcined form, contains from about 1 to about 100 ppm by weight of a halide.

41. The process of claim 37 wherein said material, in its calcined form, contains from about 5 to about 50 ppm by weight of a halide.

42. The process of claim 37 wherein said material, in its calcined form, contains from about 10 to about 20 ppm, by weight of a halide.

43. The process of claim 37 wherein said halide comprises fluoride.

44. The process of claim 37 wherein n is from about 0.001 to less than 0.01.

45. The process of claim 37 wherein n is from about 0.0025 to about 0.008.

46. The process of claim 37 wherein n is from about 0.003 to about 0.007.

47. The process of claim 38 wherein said organic oxygenate compound comprises methanol, dimethyl ether or a mixture thereof.

* * * * *